United States Patent
Qi et al.

(10) Patent No.: US 11,529,067 B2
(45) Date of Patent: Dec. 20, 2022

(54) SECURITY CHECK METHOD AND SYSTEM BASED ON MICROWAVE IMAGING OF HUMAN BODIES

(71) Applicants: CHINA COMMUNICATION TECHNOLOGY CO., LTD., Shenzhen (CN); SHENZHEN INSTITUTE OF TERAHERTZ TECHNOLOGY AND INNOVATION, Shenzhen (CN)

(72) Inventors: Chunchao Qi, Shenzhen (CN); Aixian Wang, Shenzhen (CN); Hanjiang Chen, Shenzhen (CN); Tiansheng Zhang, Shenzhen (CN); Zhihui Feng, Shenzhen (CN); Hu Yuan, Shenzhen (CN); Shukai Zhao, Shenzhen (CN)

(73) Assignees: CHINA COMMUNICATION TECHNOLOGY CO., LTD., Shenzhen (CN); SHENZHEN INSTITUTE OF TERAHERTZ TECHNOLOGY AND INNOVATION, Shenzhen (CN)

( * ) Notice: Subject to any disclaimer, the term of this patent is extended or adjusted under 35 U.S.C. 154(b) by 904 days.

(21) Appl. No.: 16/345,985

(22) PCT Filed: Aug. 4, 2017

(86) PCT No.: PCT/CN2017/096109
§ 371 (c)(1),
(2) Date: Apr. 29, 2019

(87) PCT Pub. No.: WO2018/076885
PCT Pub. Date: May 3, 2018

(65) Prior Publication Data
US 2020/0054236 A1 Feb. 20, 2020

(30) Foreign Application Priority Data
Oct. 31, 2016 (CN) .......................... 201610931147.1

(51) Int. Cl.
*A61B 5/0507* (2021.01)
*G01N 23/04* (2018.01)
(Continued)

(52) U.S. Cl.
CPC ............ *A61B 5/0507* (2013.01); *G01N 23/04* (2013.01); *G01S 13/887* (2013.01); *G06T 7/70* (2017.01); *G01N 2223/33* (2013.01)

(58) Field of Classification Search
CPC ....... G01S 13/887; G01V 3/12; A61B 5/0507; G01N 23/04; G01N 2223/33; G06T 7/70; H01J 2237/221
See application file for complete search history.

(56) References Cited

U.S. PATENT DOCUMENTS

2006/0109174 A1    5/2006   Baharav et al.

FOREIGN PATENT DOCUMENTS

CN    101937425 A    1/2011
CN    102393537 A    3/2012
(Continued)

*Primary Examiner* — Bernarr E Gregory
*Assistant Examiner* — Oladimeji Oyegunle
(74) *Attorney, Agent, or Firm* — FisherBroyles, LLP; Jason P. Mueller (57) ABSTRACT

A security check method includes: pre-creating at least four concurrently operating threads, one thread being responsible for movement control and data acquisition, one thread being responsible for imaging processing, one thread being responsible for interface displaying, and one thread being responsible for target detection and recognition; then the four concurrently operating threads divide original echo data of a human body to be checked into data of a plurality of adjacent overlapped azimuthal segments during data processing and perform individual processing on the data of each azimuthal segment. The security check system includes a thread creating unit, a first thread parallel unit, a second
(Continued)

thread parallel unit, a third thread parallel unit, a fourth thread parallel unit, and a thread loop control unit. Because subsequent data processing is not required to be performed after the acquisition of all data is completed, the time for a security check process is reduced.

15 Claims, 4 Drawing Sheets

(51) Int. Cl.
  *G06T 7/70* (2017.01)
  *G01S 13/88* (2006.01)

(56) References Cited

FOREIGN PATENT DOCUMENTS

| | | | | |
|---|---|---|---|---|
| CN | 102426361 A | * | 4/2012 | |
| CN | 102426361 A | | 4/2012 | |
| CN | 102508240 A | | 6/2012 | |
| CN | 102508306 A | | 6/2012 | |
| CN | 102508307 A | | 6/2012 | |
| CN | 105759269 A | | 7/2016 | |
| CN | 106556873 A | | 4/2017 | |
| WO | WO-2012048173 A2 | * | 4/2012 | ............... H04N 7/18 |

* cited by examiner

SECURITY CHECK METHOD AND SYSTEM BASED ON MICROWAVE IMAGING OF HUMAN BODIES

CROSS-REFERENCE TO RELATED APPLICATIONS

This application is a national stage entry under 35 U.S.C. 371 of PCT Patent Application No. PCT/CN2017/096109, filed Aug. 4, 2017, which claims priority to Chinese Patent Application No. 201610931147.1, filed Oct. 31, 2016, the entire contents of each of which is incorporated herein by reference.

TECHNICAL FIELD

This disclosure relates to the technical field of security check, in particular to a security check method and system based on microwave imaging of human bodies.

BACKGROUND

A close-range human body three-dimensional scan-imaging security check system can identify prohibited goods hidden on a human body by scanning microwaves, millimeter waves or terahertz waves emitted by the human body. At present, the close-range human body three-dimensional scan-imaging security check system is widely used in airports, courts and other places requiring security check of personnel. The close-range human body three-dimensional scan-imaging security check systems can be divided into flat scanning systems and cylindrical scanning systems according to a scanning surface formed by phase centers of transceiver antenna units, wherein the cylindrical scanning systems use an array antenna to surround a detected human body so as to obtain electromagnetic scattering information of the human body from multiple angles, and are the main form of the close-range human body three-dimensional scan-imaging security check systems. However, at present, when the cylindrical scanning systems are used for security check, all the acquired original echoes can be obtained only after rotate-scanning by the array antenna is completed, and then an imaging result can be obtained for subsequent dangerous goods target detection, recognition and display after the original echoes are imaged; and the whole process of data acquisition, imaging processing and display is a serial execution process, and a security check process on human bodies requires a long time and is low in efficiency, which cannot meet the real-time requirements of a security check under the condition of a large flow of people.

BRIEF SUMMARY

The embodiment of the disclosure aims to provide a security check method and system based on microwave imaging of human bodies, so as to solve the problem that a security check process on human bodies by a cylindrical scanning system requires a long time and is low in efficiency, which cannot meet the real-time requirements of security check under the condition of a large flow of people.

The embodiment of the disclosure is realized as follows: the security check method based on microwave imaging of human bodies includes:

pre-creating at least four concurrently operating threads, one thread being responsible for movement control and data acquisition, one thread being responsible for imaging processing, one thread being responsible for interface displaying, and one thread being responsible for target detection and recognition;

controlling, by the thread responsible for movement control and data acquisition, a security check system to gradually acquire echo data of a human body to be checked at 0-2π azimuth angles and to gradually transmit the echo data to a memory of the security check system;

instructing, by the thread responsible for movement control and data acquisition, according to a current data acquisition state in the process of gradually acquiring the echo data, the thread responsible for imaging processing to read from the memory echo data within an azimuth angle corresponding to a current frame of image;

performing three-dimensional imaging processing on the read echo data in the thread responsible for imaging processing, to obtain three-dimensional imaging complex image data of the human body to be checked, and synchronously transmitting the three-dimensional imaging complex image data to the thread responsible for interface displaying and the thread responsible for target detection and recognition;

processing the three-dimensional imaging complex image data in the thread responsible for interface displaying, and displaying a formed image obtained after the processing on a human-computer interaction interface; meanwhile, performing hidden article target detection on the three-dimensional imaging complex image data in the thread responsible for detection and recognition, and identifying a detected article and then feeding back a detection and identification result to the thread responsible for interface displaying, so that the thread responsible for detection and recognition marks a position of the hidden article at the human body and a type of the hidden article on the formed image according to the detection and identification result; and returning to the stage of instructing, by the thread responsible for movement control and data acquisition, according to the current data acquisition state in the process of gradually acquiring the echo data, the thread responsible for imaging processing to read from the memory echo data within the azimuth angle corresponding to the current frame of image, and repeating the above stages until the processing and the displaying of the $N^{th}$ frame of image are completed according to a preset rule, the obtained N frames of images covering the echo data of the human body to be checked at the 0-2π azimuth angles, N being a positive integer.

On the basis of the above technical scheme, the stage of gradually transmitting the echo data to the memory of the security check system specifically includes:

dividing the echo data of the human body to be checked at the 0-2π azimuth angles into N adjacent overlapped equal-length intervals, and transmitting and storing the echo data of the N equal-length intervals one by one to the memory of the security check system according to the order of the azimuth angles.

On the basis of the above technical scheme, the stage of instructing, by the thread responsible for movement control and data acquisition, according to the current data acquisition state in the process of gradually acquiring the echo data, the thread responsible for imaging processing to read from the memory echo data within the azimuth angle corresponding to the current frame of image specifically includes:

sending, by the thread responsible for movement control and data acquisition, a notification to the thread responsible for imaging processing every time the echo data of one of the equal-length intervals is written into the memory in the process of gradually acquiring the echo data, the notification comprising an identifier of the equal-length interval whose echo data is currently written into the memory, so that the thread responsible for imaging processing reads the echo data within a corresponding azimuth angle according to the identifier.

On the basis of the above technical scheme, the value of N is 18, and the length of each equal-length interval is $\pi/2$ radian.

On the basis of the above technical scheme, the stage of performing three-dimensional imaging processing on the read echo data in the thread responsible for imaging processing to obtain the three-dimensional imaging complex image data of the human body to be checked specifically includes:

controlling, in the thread responsible for imaging processing, a graphics processing card in the security check system to perform the three-dimensional imaging processing on the echo data by using a three-dimensional distance migration algorithm or a three-dimensional distance stack algorithm to obtain the three-dimensional imaging complex image data of the human body to be checked.

Another object of the embodiment of the present disclosure is to provide a security check system based on the microwave imaging of human bodies, comprising:

a thread creating unit, configured to perform operations including pre-creating at least four concurrently operating threads, one thread being responsible for movement control and data acquisition, one thread being responsible for imaging processing, one thread being responsible for interface displaying, and one thread being responsible for target detection and recognition;

a first thread parallel unit, configured to perform operations including controlling, by the thread responsible for movement control and data acquisition, the security check system to gradually acquire echo data of a human body to be checked at 0-$2\pi$ azimuth angles and to gradually transmit the echo data to a memory of the security check system; the thread responsible for movement control and data acquisition instructing, according to a current data acquisition state in the process of gradually acquiring the echo data, the thread responsible for imaging processing to read from the memory echo data within an azimuth angle corresponding to a current frame of image;

a second thread parallel unit, configured to perform operations including performing three-dimensional imaging processing on the read echo data in the thread responsible for imaging processing to obtain three-dimensional imaging complex image data of the human body to be checked, and synchronously transmitting the three-dimensional imaging complex image data to the thread responsible for interface displaying and the thread responsible for target detection and recognition;

a third thread parallel unit, configured to perform operations including processing the three-dimensional imaging complex image data in the thread responsible for interface displaying, and displaying a formed image obtained after the processing on a human-computer interaction interface; meanwhile, a fourth thread parallel unit, configured to perform operations including performing hidden article target detection on the three-dimensional imaging complex image data in the thread responsible for detection and recognition, and identifying a detected article and then feeding back a detection and identification result to the thread responsible for interface displaying, so that the thread responsible for detection and recognition marks a position of the hidden article at the human body and a type of the hidden article on the formed image according to the detection and identification result; and a thread loop control unit, configured to perform operations including controlling the first thread parallel unit, the second thread parallel unit, the third thread parallel unit and the fourth thread parallel unit to repeat the above stages until the processing and the displaying of the $N^{th}$ frame of image are completed according to a preset rule, the obtained N frames of images covering the echo data of the human body to be checked at the 0-$2\pi$ azimuth angles, N being a positive integer.

On the basis of the above technical scheme, the first thread parallel unit includes:

an equal-length interval dividing unit, configured to perform operations including dividing the echo data of the human body to be checked at the 0-$2\pi$ azimuth angles into N adjacent overlapped equal-length intervals, and transmitting and storing the echo data of the N equal-length intervals one by one to the memory of the security check system according to the order of the azimuth angles.

On the basis of the above technical scheme, the first thread parallel unit includes:

a current data acquisition notification unit, configured to perform operations including sending, by the thread responsible for movement control and data acquisition, a notification to the thread responsible for imaging processing every time the echo data of one of the equal-length intervals is written into the memory in the process of gradually acquiring the echo data, the notification comprising an identifier of the equal-length interval whose the echo data is currently written into the memory, so that the thread responsible for imaging processing reads the echo data within a corresponding azimuth angle according to the identifier.

On the basis of the above technical scheme, the value of N is 18, and the length of each equal-length interval is $\pi/3$ radian.

On the basis of the above technical scheme, the second thread parallel unit is specifically configured to perform operations including:

controlling, in the thread responsible for imaging processing, a graphics processing card in the security check system to perform the three-dimensional imaging processing on the echo data by using a three-dimensional distance migration algorithm or a three-dimensional distance stack algorithm to obtain the three-dimensional imaging complex image data of the human body to be checked.

The security check method and system based on microwave imaging of human bodies provided by the embodiment of the disclosure have the following beneficial effect:

according to the embodiment of the disclosure, at least four concurrently operating threads are pre-created, one thread is responsible for movement control and data acquisition, one thread is responsible for imaging processing, one thread is responsible for interface displaying, and one thread is responsible for target detection and recognition; and then the four concurrently operating threads divide the acquired 360-degree original echo data of the human body to be checked into data of a plurality of adjacent overlapped azimuthal segments during data processing and perform individual processing on the data of each azimuthal segment, so that subsequent data processing is not required to be performed after the acquisition of all data is completed, the time for a security check process is reduced, security check efficiency is improved, and the real-time requirement of security check under the condition of a large flow of people can be met.

DETAILED DESCRIPTION

In order to make the object, technical scheme and advantages of the disclosure clearer, the disclosure will be described in further detail below with reference to the drawings and embodiments. It should be understood that the specific embodiments described herein are only used to illustrate the disclosure and are not configured to limit the disclosure.

Figure 1:
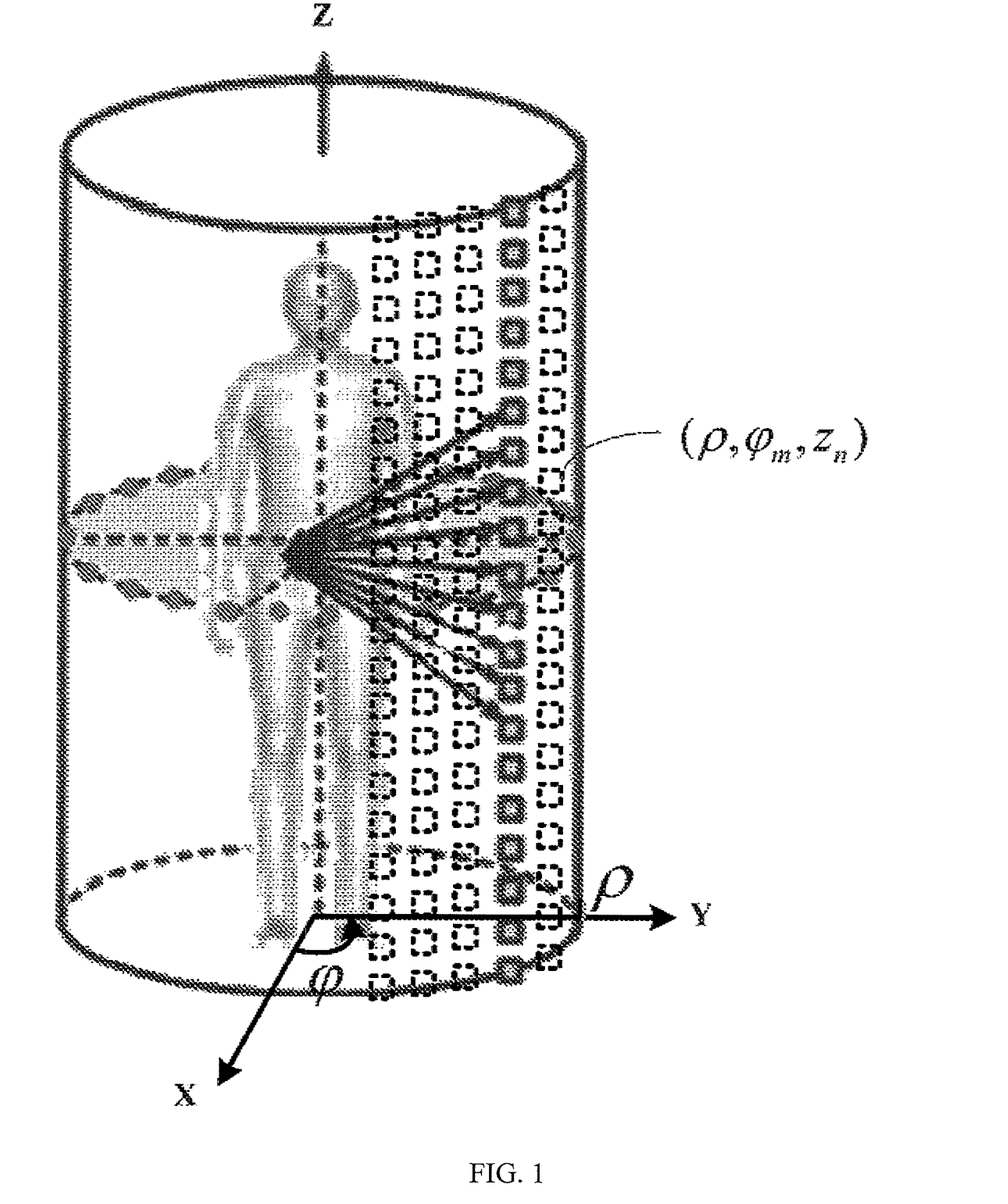
FIG. 1 is a geometric schematic diagram of cylindrical scanning of a security check system based on microwave imaging of human bodies provided by the embodiment of the disclosure.

FIG. 1 is a geometric schematic diagram of cylindrical scanning of a security check system based on microwave imaging of human bodies in the embodiment of the disclosure. Referring to FIG. 1, transceiver antenna units form a linear array in a vertical height Z direction with a distance p from a central axis of a cylindrical scanning set; meanwhile, the linear array is rotationally scanned and finally equivalently forms a plurality of antenna equivalent phase centers with equal anti-counterfeiting intervals and equal height direction coordinates distributed on a cylindrical surface. A position of a certain antenna phase center is represented by cylindrical coordinates $(\rho, \phi_m, z_n)$, wherein $\phi_m$ represents an azimuth coordinate value of an $m^{th}$ azimuth direction sampling point under the condition of equal-interval sampling in an azimuth direction, $0 \leq m \leq M-1$, wherein M represents a total number of points scanned in the azimuth direction by the antenna phase center; and $z_n$ represents a height coordinate value of an $N^{th}$ height direction sampling point under the condition of equal-interval sampling in a height direction, $0 \leq n \leq P-1$, wherein P represents a total number of points scanned in the height direction by the antenna phase center. Human body microwave three-dimensional echo simulation is to calculate echo data at all antenna phase centers $(\rho, \phi_m, z_n)$ by means of data simulation.

Figure 2:
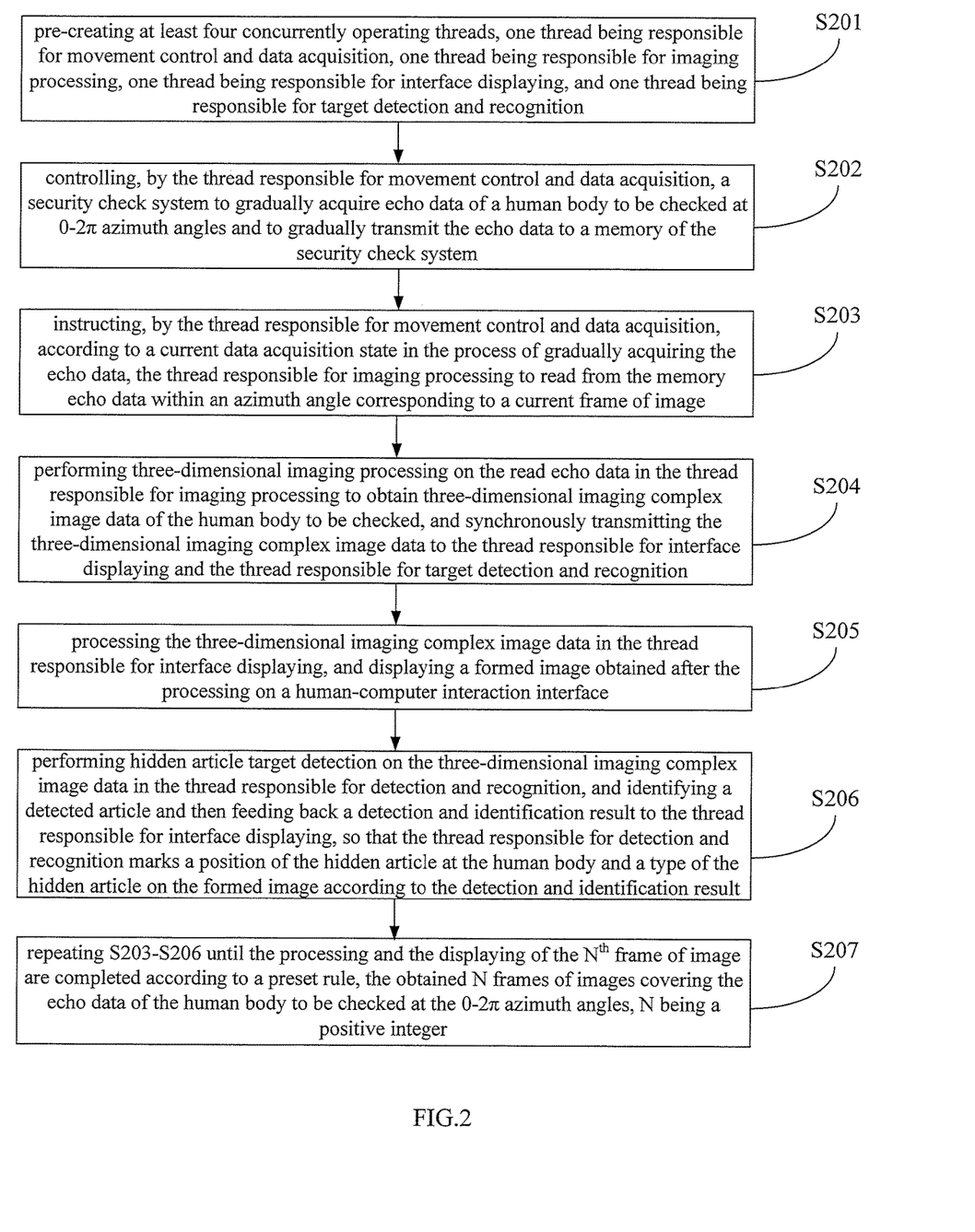
FIG. 2 is a schematic flow chart of a security check method based on microwave imaging of human bodies provided by the embodiment of the disclosure.

FIG. 2 is a schematic flow chart of a security check method based on microwave imaging of human bodies provided by the embodiment of the disclosure. Referring to FIG. 2, the method may include the following stages:

S201, pre-creating at least four concurrently operating threads, one thread being responsible for movement control and data acquisition, one thread being responsible for imaging processing, one thread being responsible for interface displaying, and one thread being responsible for target detection and recognition.

In this embodiment, the thread responsible for movement control and data acquisition, the thread responsible for imaging processing, the thread responsible for interface displaying and the thread responsible for target detection and recognition are four concurrently operating threads and are responsible for performing different tasks.

S202, controlling, by the thread responsible for movement control and data acquisition, a security check system to gradually acquire echo data of a human body to be checked at 0-2π azimuth angles and to gradually transmit the echo data to a memory of the security check system.

In this embodiment, the stage of gradually transmitting the echo data to the memory of the security check system specifically includes: dividing the echo data of the human body to be checked at the 0-2π azimuth angles into N adjacent overlapped equal-length intervals, and transmitting the echo data of the N equal-length intervals one by one according to the order of the azimuth angles to the memory of the security check system and storing them therein.

Figure 3:
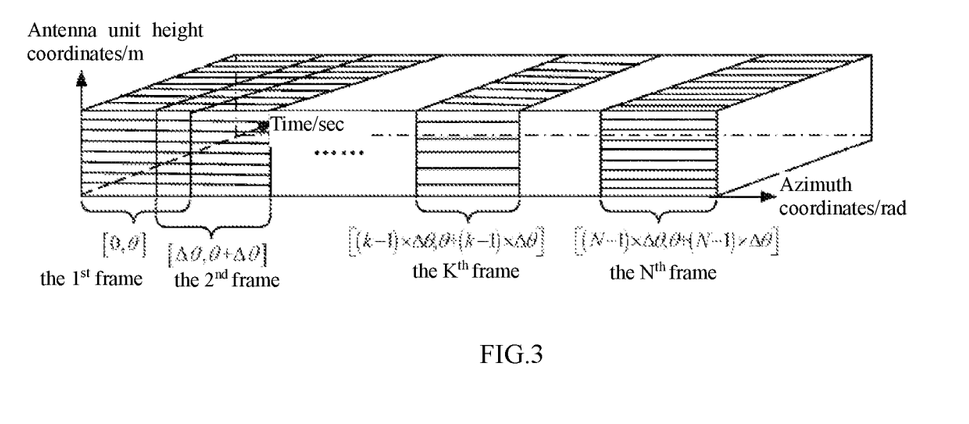
FIG. 3 is a schematic diagram of dividing echo data at 0-2π azimuth angles into segment data of N equal-length intervals in a security check method based on microwave imaging of human bodies provided by the embodiment of the disclosure.

As shown in FIG. 3, in this embodiment, the value of the length of each interval is set to be θ radian, then the starting ends of two adjacent intervals are separated from each other by $\Delta\theta=(360-\theta)/(N-1)$ radian, and so the N intervals are sequentially $[0, \theta]$, $[\Delta\theta, \Delta\theta+\theta]$, ..., $[(k-1)\times\Delta\theta, \theta+(k-1)\times\Delta\theta]$, $[(N-1)\times\Delta\theta, \theta+(N-1)\times\Delta\theta]$.

Further, in this embodiment, the value of θ is π/3 radian, and the value of N is 18.

S203, instructing, by the thread responsible for movement control and data acquisition, according to a current data acquisition state in the process of gradually acquiring the echo data, the thread responsible for imaging processing to read from the memory echo data within an azimuth angle corresponding to a current frame of image.

In this embodiment, S203 specifically includes: sending, by the thread responsible for movement control and data acquisition, a notification to the thread responsible for imaging processing every time the echo data of one equal-length interval is written into the memory in the process of gradually acquiring the echo data, the notification comprising an identifier of the equal-length interval in which the echo data is currently written into the memory, so that the thread responsible for imaging processing reads the echo data within the corresponding azimuth angle according to the identifier.

In this embodiment, the echo data of each equal-length interval correspondingly generates one frame of formed image. When reading the echo data from the security check system, the thread responsible for imaging processing firstly determines a frame number of a current image to be imaged among N frames of images of a human body target according to the identifier in the currently received notification, and if it is the $k^{th}$ frame, reads the echo data corresponding to the $k^{th}$ azimuth interval range $[(k-1)\times\Delta\theta, \theta+(k-1)\times\Delta\theta]$; for imaging processing, wherein k is a positive integer greater than 0 and less than or equal to N.

S204, performing three-dimensional imaging processing on the read echo data in the thread responsible for imaging processing to obtain three-dimensional imaging complex image data of the human body to be checked, and synchronously transmitting the three-dimensional imaging complex image data to the thread responsible for interface displaying and the thread responsible for target detection and recognition.

In this embodiment, the stage of performing three-dimensional imaging processing on the read echo data in the thread responsible for imaging processing to obtain the three-dimensional imaging complex image data of the human body to be checked specifically includes:

controlling, in the thread responsible for imaging, a graphics processing card in the security check system processing to perform the three-dimensional imaging processing on the echo data by using a three-dimensional distance migration algorithm or a three-dimensional distance stack algorithm to obtain the three-dimensional imaging complex image data of the human body to be checked.

S205, processing the three-dimensional imaging complex image data in the thread responsible for interface displaying, and displaying a formed image obtained after the processing on a human-computer interaction interface; meanwhile, S206, performing hidden article target detection on the three-dimensional imaging complex image data in the thread responsible for detection and recognition, and identifying a detected article and then feeding back a detection and identification result to the thread responsible for interface displaying, so that the thread responsible for detection and recognition marks a position of the hidden article at the human body and a type of the hidden article on the formed image according to the detection and identification result.

In this embodiment, during the concurrent operations of the above four threads, the thread responsible for interface displaying keeps monitoring an antenna scanning movement state, a data acquisition state and an imaging processing progress state of a key system fed back from other threads, and displays the monitored states on the human-computer interaction interface in real time in a visual manner. When it is detected that the thread responsible for imaging processing has completed the imaging processing of one frame of image, the corresponding three-dimensional imaging complex image data of the human body is subjected to processing such as amplitude calculation, fuzzy processing of private parts and rendering, and the processed image is displayed on the human-computer interaction interface.

In this embodiment, S205 and S206 are carried out at the same time. The thread responsible for detection and recognition feeds back the detection and identification result to the thread responsible for interface display processing after carrying out target detection and identification on the hidden article; at this time, the thread responsible for interface display processing displays the target detection and identification result on the formed image displayed on the human-computer interaction interface in a visual or text mark manner, so that security personnel can visually obtain the position of the hidden article on the human body to be checked and the type of the hidden article.

S207, repeating S203-S206 until the processing and the displaying of the $N^{th}$ frame of image are completed according to a preset rule, the obtained N frames of images covering the echo data of the human body to be checked at the 0-2π azimuth angles, N being a positive integer.

It can be seen from above that according to the security check method based on microwave imaging of human bodies provided by the embodiment, at least four concurrently operating threads are pre-created, one thread is responsible for movement control and data acquisition, one thread is responsible for imaging processing, one thread is responsible for interface displaying, and one thread is responsible for target detection and recognition; and then the four concurrently operating threads divide the acquired 360-degree original echo data of the human body to be checked into data of a plurality of adjacent overlapped azimuthal segments during data processing and perform individual processing on the data of each azimuthal segment, so that subsequent data processing is not required to be performed after the acquisition of all data is completed, the time for a security check process is reduced, security check efficiency is improved and the real-time requirement of security check under the condition of a large flow of people can be met.

Figure 4:
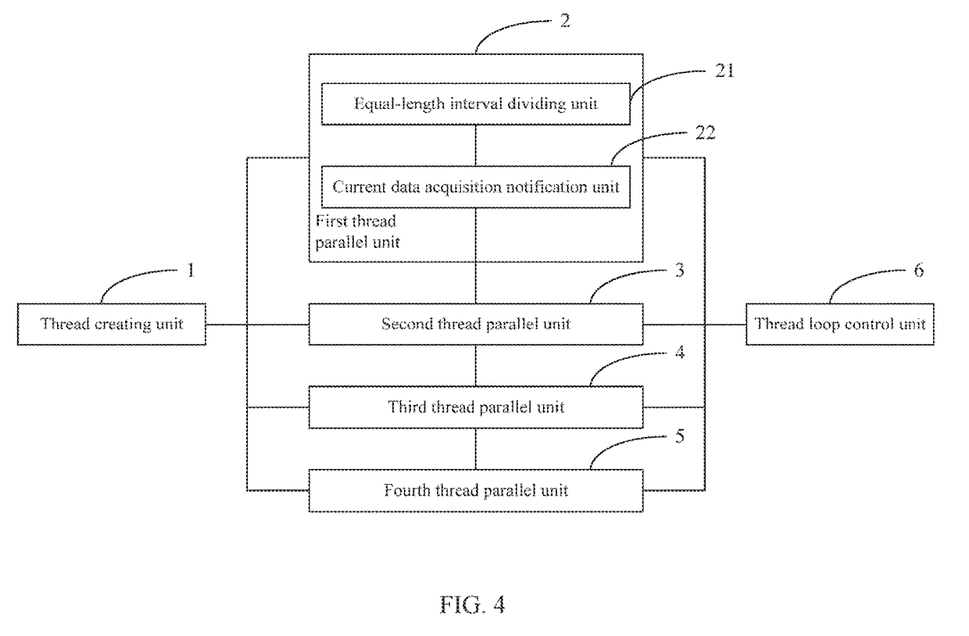
FIG. 4 is a schematic block diagram of a security check system based on microwave imaging of human bodies provided by the embodiment of the disclosure.

FIG. 4 is a schematic block diagram of a security check system based on microwave imaging of human bodies provided by the embodiment of the disclosure, and the system is the executive body of the security check method provided in the embodiment shown in FIG. 2. For convenience of explanation, only parts related to the present embodiment are shown.

Referring to FIG. 4, a security check system based on microwave imaging of human bodies provided by the embodiment includes:

a thread creating unit 1, configured to perform operations including pre-creating at least four concurrently operating threads, one thread being responsible for movement control and data acquisition, one thread being responsible for imaging processing, one thread being responsible for interface displaying, and one thread being responsible for target detection and recognition;

a first thread parallel unit 2, configured to perform operations including controlling, by the thread responsible for movement control and data acquisition, the security check system to gradually acquire echo data of a human body to be checked at 0-2π azimuth angles and to gradually transmit the echo data to a memory of the security check system; the thread responsible for movement control and data acquisition instructing, according to a current data acquisition state in the process of gradually acquiring the echo data, the thread responsible for imaging processing to read from the memory echo data within an azimuth angle corresponding to a current frame of image;

a second thread parallel unit 3, configured to perform operations including performing three-dimensional imaging processing on the read echo data in the thread responsible for imaging processing to obtain three-dimensional imaging complex image data of the human body to be checked, and synchronously transmitting the three-dimensional imaging complex image data to the thread responsible for interface displaying and the thread responsible for target detection and recognition;

a third thread parallel unit 4, configured to perform operations including processing the three-dimensional imaging complex image data in the thread responsible for interface displaying, and displaying a formed image obtained after the processing on a human-computer interaction interface; meanwhile, a fourth thread parallel unit 5, configured to perform operations including performing hidden article target detection on the three-dimensional imaging complex image data in the thread responsible for detection and recognition, and identifying a detected article and then feeding back a detection and identification result to the thread responsible for interface displaying, so that the thread responsible for detection and recognition marks a position of the hidden article at the human body and a type of the hidden article on the formed image according to the detection and identification result; and a thread loop control unit 6, configured to perform operations including controlling the first thread parallel unit, the second thread parallel unit, the third thread parallel unit and the fourth thread parallel unit to repeat the above stages until the processing and the displaying of the $N^{th}$ frame of image are completed according to a preset rule, the obtained N frames of images covering the echo data of the human body to be checked at the 0-2π azimuth angles, N being a positive integer.

Optionally, the first thread parallel unit 2 includes:

an equal-length interval dividing unit 21, configured to perform operations including dividing the echo data of the human body to be checked at the 0-2π azimuth angles into N-adjacent overlapped equal-length intervals, and transmitting the echo data of the N equal-length intervals one by one according to the order of the azimuth angles to the memory of the security check system and storing them therein.

Optionally, the first thread parallel unit 2 includes:

a current data acquisition notification unit 22, configured to perform operations including sending, by the thread responsible for movement control and data acquisition, a notification to the thread responsible for imaging processing every time the echo data of one equal-length interval is written into the memory in the process of gradually acquiring the echo data, the notification comprising an identifier of the equal-length interval in which the echo data is currently written into the memory, so that the thread responsible for imaging processing reads the echo data within the corresponding azimuth angle according to the identifier.

Optionally, the value of N is 18, and the length of each equal-length interval is π/3 radian.

Optionally, the second thread parallel unit 3 is specifically configured to perform operations including:

controlling, in the thread responsible for imaging, a graphics processing card in the security check system processing to perform the three-dimensional imaging processing on the echo data by using a three-dimensional distance migration algorithm or a three-dimensional distance stack algorithm, to obtain the three-dimensional imaging complex image data of the human body to be checked.

It should be noted that each unit in the above-mentioned system provided by the embodiment of the disclosure has the same technical effect as the embodiment of the method of the disclosure because it is based on the same concept as the embodiment of the method of the disclosure. The specific content can be seen in the description of the embodiment of the method of the disclosure and will not be repeated here.

Therefore, it can be seen that according to the security check system based on microwave imaging of human bodies provided by the embodiment, the time for a security check process can be reduced, security check efficiency can be improved, and the real-time requirement of security check under the condition of a large flow of people can be met.

The above-described embodiment is not intended to limit the disclosure. Any modifications, equivalent substitutions, improvements, etc. made within the spirit and principles of the disclosure should be included within the scope of protection of the disclosure.

What is claimed is:

1. A processor implemented security check method based on microwave imaging of human bodies, the method comprising:

pre-creating, by a multithreading processor circuit, at least four concurrently operating threads, one of the threads being responsible for movement control and data acquisition, one of the threads being responsible for imaging processing, one of the threads being responsible for interface displaying, and one of the threads being responsible for target detection and recognition;

controlling, by the thread responsible for movement control and data acquisition, a security check system to gradually acquire echo data of a human body to be checked at a plurality of azimuth angles within an angular range of 0-2π and to gradually transmit the echo data to a memory of the security check system;

instructing, by the thread responsible for movement control and data acquisition according to a current data acquisition state in a process of gradually acquiring the echo data, the thread responsible for imaging processing to read, from the memory, echo data within an azimuth angle corresponding to a current frame of image;

performing three-dimensional imaging processing on the read echo data, in the thread responsible for imaging processing, to obtain three-dimensional imaging complex image data of the human body to be checked, and synchronously transmitting the three-dimensional imaging complex image data to the thread responsible for interface displaying and to the thread responsible for target detection and recognition;

processing the three-dimensional imaging complex image data in the thread responsible for interface displaying, and displaying a formed image, obtained after the processing, on a human-computer interaction interface; meanwhile, performing hidden article target detection on the three-dimensional imaging complex image data in the thread responsible for detection and recognition, identifying a detected article, and then feeding back a detection and identification result to the thread responsible for interface displaying, so that the thread responsible for interface displaying marks a position of the hidden article at the human body and a type of the hidden article on the formed image according to the detection and identification result; and returning to the stage of instructing, by the thread responsible for movement control and data acquisition according to the current data acquisition state in a process of gradually acquiring the echo data, the thread responsible for imaging processing to read, from the memory, echo data within the azimuth angle corresponding to the current frame of image, and repeating the above stages until the processing and the displaying of an $N^{th}$ frame of image are completed according to a preset rule, to thereby obtain N frames of images covering the echo data of the human body to be checked at the plurality of azimuth angles within the angular range of 0-2π, with N being a positive integer.

2. The method according to claim 1, wherein the stage of gradually transmitting the echo data to the memory further comprises:

dividing the echo data of the human body to be checked at the plurality of azimuth angles within the angular range of 0-2π into N adjacent overlapped equal-length intervals, and transmitting and storing the echo data of the N equal-length intervals one by one to the memory according to an order of the azimuth angles.

3. The method according to claim 2, wherein the stage of instructing, by the thread responsible for movement control and data acquisition according to the current data acquisition state in a process of gradually acquiring the echo data, the thread responsible for imaging processing to read, from the memory, echo data within the azimuth angle corresponding to the current frame of image further comprises:

sending, by the thread responsible for movement control and data acquisition, a notification to the thread responsible for imaging processing every time the echo data of one of the equal-length intervals is written into the memory in the process of gradually acquiring the echo data, the notification comprising an identifier of the equal-length interval whose echo data is currently written into the memory, so that the thread responsible for imaging processing reads the echo data within a corresponding azimuth angle according to the identifier.

4. The method according to claim 2, wherein a value of N is 18, and a length of each of the equal-length intervals is $\pi/3$ radian.

5. The method according to claim 1, wherein the stage of performing three-dimensional imaging processing on the read echo data in the thread responsible for imaging processing to obtain three-dimensional imaging complex image data of the human body to be checked further comprises:
controlling, in the thread responsible for imaging processing, a graphics processing card in the security check system to perform the three-dimensional imaging processing on the echo data by using a three-dimensional distance migration algorithm or a three-dimensional distance stack algorithm to obtain the three-dimensional imaging complex image data of the human body to be checked.

6. A security check system based on microwave imaging of human bodies, comprising:
a memory; and
a multithreading processor circuit configured to perform operations comprising:
pre-creating at least four concurrently operating threads, one of the threads being responsible for movement control and data acquisition, one of the threads being responsible for imaging processing, one of the threads being responsible for interface displaying, and one of the threads being responsible for target detection and recognition;
controlling, by the thread responsible for movement control and data acquisition, a security check system to gradually acquire echo data of a human body to be checked at a plurality of azimuth angles in an angular range of $0-2\pi$ and to gradually transmit the echo data to the memory;
instructing, by the thread responsible for movement control and data acquisition according to a current data acquisition state in a process of gradually acquiring the echo data, the thread responsible for imaging processing to read, from the memory, echo data within an azimuth angle corresponding to a current frame of image;
performing three-dimensional imaging processing on the read echo data in the thread responsible for imaging processing to obtain three-dimensional imaging complex image data of the human body to be checked, and synchronously transmitting the three-dimensional imaging complex image data to the thread responsible for interface displaying and the thread responsible for target detection and recognition;
processing the three-dimensional imaging complex image data in the thread responsible for interface displaying, and displaying a formed image obtained after the processing on a human-computer interaction interface; meanwhile,
performing hidden article target detection on the three-dimensional imaging complex image data in the thread responsible for detection and recognition, identifying a detected article, and then feeding back a detection and identification result to the thread responsible for interface displaying, so that the thread responsible for interface displaying marks a position of the hidden article at the human body and a type of the hidden article on the formed image according to the detection and identification result; and
returning to the stage of instructing, by the thread responsible for movement control and data acquisition according to a current data acquisition state in a process of gradually acquiring the echo data, the thread responsible for imaging processing to read, from the memory, echo data within the azimuth angle corresponding to the current frame of image, and repeating the above stages until the processing and the displaying of an $N^{th}$ frame of image are completed according to a preset rule, to thereby obtain N frames of images covering the echo data of the human body to be checked at the plurality of azimuth angles in the range of $0-2\pi$, with N being a positive integer.

7. The system according to claim 6, wherein the multithreading processor circuit is further configured to perform operations relating to the stage of gradually transmitting the echo data to the memory, the operations further comprising:
dividing the echo data of the human body to be checked at the plurality of azimuth angles in the angular range of $0-2\pi$ into N adjacent overlapped equal-length intervals, and transmitting and storing the echo data of the N equal-length intervals one by one to the memory according to an order of the azimuth angles.

8. The system according to claim 7, wherein the multithreading processor circuit is further configured to perform operations relating to the stage of instructing, by the thread responsible for movement control and data acquisition according to the current data acquisition state in a process of gradually acquiring the echo data, the thread responsible for imaging processing to read from the memory echo data within the azimuth angle corresponding to the current frame of image, the operations further comprising:
sending, by the thread responsible for movement control and data acquisition, a notification to the thread responsible for imaging processing, every time the echo data of one of the equal-length intervals is written into the memory in the process of gradually acquiring the echo data, the notification comprising an identifier of the equal-length interval whose echo data is currently written into the memory, so that the thread responsible for imaging processing reads the echo data within a corresponding azimuth angle according to the identifier.

9. The system according to claim 7, wherein a value of N is 18, and a length of each of the equal-length intervals is $\pi/3$ radian.

10. The system according to claim 6, wherein the multithreading processor circuit is further configured to perform operations relating to the stage of performing three-dimensional imaging processing on the read echo data in the thread responsible for imaging processing to obtain three-dimensional imaging complex image data of the human body to be checked, the operations further comprising:
controlling, in the thread responsible for imaging processing, a graphics processing card in the security check system to perform the three-dimensional imaging processing on the echo data by using a three-dimensional distance migration algorithm or a three-dimensional distance stack algorithm to obtain the three-dimensional imaging complex image data of the human body to be checked.

11. A non-transitory computer storage medium storing a computer program, which when executed by one or more multithreading processors, causes the one or more multithreading processor circuits to perform operations comprising:
pre-creating at least four concurrently operating threads, one of the threads being responsible for movement control and data acquisition, one of the threads being responsible for imaging processing, one of the threads being responsible for interface displaying, and one of the threads being responsible for target detection and recognition;

controlling, by the thread responsible for movement control and data acquisition, a security check system to gradually acquire echo data of a human body to be checked at a plurality of azimuth angles in an angular range of 0-2π and to gradually transmit the echo data to a memory of the security check system;

instructing, by the thread responsible for movement control and data acquisition according to a current data acquisition state in a process of gradually acquiring the echo data, the thread responsible for imaging processing to read from the memory echo data within an azimuth angle corresponding to a current frame of image;

performing three-dimensional imaging processing on the read echo data in the thread responsible for imaging processing to obtain three-dimensional imaging complex image data of the human body to be checked, and synchronously transmitting the three-dimensional imaging complex image data to the thread responsible for interface displaying and the thread responsible for target detection and recognition;

processing the three-dimensional imaging complex image data in the thread responsible for interface displaying, and displaying a formed image obtained after the processing on a human-computer interaction interface; meanwhile, performing hidden article target detection on the three-dimensional imaging complex image data in the thread responsible for detection and recognition, identifying a detected article, and then feeding back a detection and identification result to the thread responsible for interface displaying, so that the thread responsible for interface displaying marks a position of the hidden article at the human body and a type of the hidden article on the formed image according to the detection and identification result; and returning to the stage of instructing, by the thread responsible for movement control and data acquisition according to a current data acquisition state in a process of gradually acquiring the echo data, the thread responsible for imaging processing to read from the memory echo data within the azimuth angle corresponding to the current frame of image, and repeating the above stages until the processing and the displaying of an $N^{th}$ frame of image are completed according to a preset rule, to thereby obtain N frames of images covering the echo data of the human body to be checked at the plurality of azimuth angles in an angular range of 0-2π azimuth angles, with N being a positive integer.

12. The non-transitory computer storage medium according to claim 11, wherein the the one or more multithreading processor circuits are configured to perform operations relating to the stage of gradually transmitting the echo data to the memory, the operations further comprising:
dividing the echo data of the human body to be checked at the plurality of azimuth angles in an angular range of 0-2π azimuth angles into N adjacent overlapped equal-length intervals, and transmitting and storing the echo data of the N equal-length intervals one by one to the memory according to an order of the azimuth angles.

13. The non-transitory computer storage medium according to according to claim 12, wherein the one or more multithreading processor circuits are configured to perform operations relating to the stage of instructing, by the thread responsible for movement control and data acquisition according to the current data acquisition state in a process of gradually acquiring the echo data, the thread responsible for imaging processing to read from the memory echo data within the azimuth angle corresponding to the current frame of image, the operations further comprising:
sending, by the thread responsible for movement control and data acquisition, a notification to the thread responsible for imaging processing every time the echo data of one of the equal-length intervals is written into the memory in the process of gradually acquiring the echo data, the notification comprising an identifier of the equal-length interval whose echo data is currently written into the memory, so that the thread responsible for imaging processing reads the echo data within a corresponding azimuth angle according to the identifier.

14. The non-transitory computer storage medium according to claim 12, wherein a value of N is 18, and a length of each of the equal-length intervals is π/3 radian.

15. The non-transitory computer storage medium according to claim 11, wherein the one or more multithreading processor circuits are configured to perform operations related to the stage of performing three-dimensional imaging processing on the read echo data in the thread responsible for imaging processing to obtain three-dimensional imaging complex image data of the human body to be checked, the operations further comprising:
controlling, in the thread responsible for imaging processing, a graphics processing card in the security check system to perform the three-dimensional imaging processing on the echo data by using a three-dimensional distance migration algorithm or a three-dimensional distance stack algorithm to obtain the three-dimensional imaging complex image data of the human body to be checked.

* * * * *